United States Patent [19]

Nguyen

[11] Patent Number: 4,966,584
[45] Date of Patent: Oct. 30, 1990

[54] SUCTION ASPIRATOR WITH NOISE-CONTROL VALVE

[76] Inventor: Long P. Nguyen, 1908 S. Church, Brenham, Tex. 77833

[21] Appl. No.: 165,126

[22] Filed: Mar. 7, 1988

Related U.S. Application Data

[63] Continuation-in-part of Ser. No. 854,551, Apr. 21, 1986, abandoned.

[51] Int. Cl.$^5$ ............................................. A61M 31/00
[52] U.S. Cl. ..................................... 604/119; 604/249; 604/902
[58] Field of Search ................. 604/119, 902, 249–250

[56] References Cited

U.S. PATENT DOCUMENTS

| | | | |
|---|---|---|---|
| 3,335,727 | 8/1967 | Spoto | 604/119 |
| 3,517,669 | 6/1970 | Buono et al. | 604/119 |
| 3,998,227 | 12/1976 | Nolbrook et al. | 604/119 |
| 4,430,073 | 2/1984 | Bemis et al. | 604/902 X |

Primary Examiner—Dalton L. Truluck

[57] ABSTRACT

The present invention is generally related to a suction aspirator for suctioning out liquids during surgical interventions. The subject suction uses a built-in interrupting valve as a means to control simultaneously the vacuum suction flow and the vacuum suction noise. The suction noise is a disturbing noise generated when a vacuum suction flow passes through the suction device. The said valve mechanism is simply constructed and easily operated by one finger of the same hand that is holding the suction device. The said valve assembly is so incorporated that it is unbiased to any working position with the suction device. The said suction device is so constructed that it can be sterilized and can be used with sterile technique required for surgery.

1 Claim, 4 Drawing Sheets

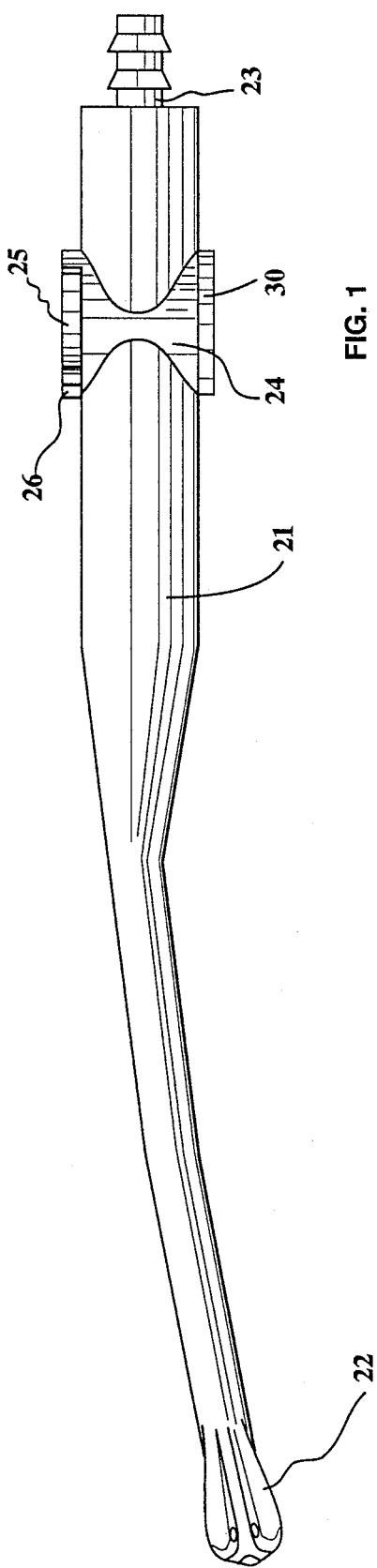
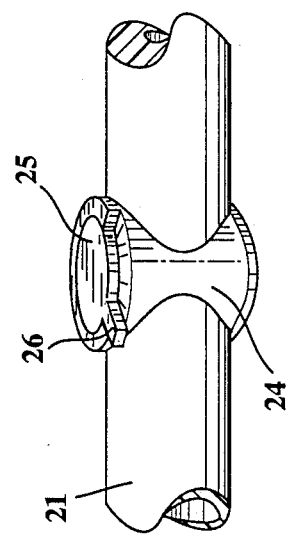
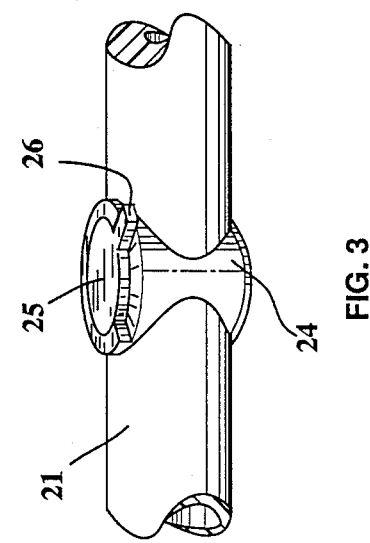
FIG. 1
FIG. 2
FIG. 3

SUCTION ASPIRATOR WITH NOISE-CONTROL VALVE

This is a continuation-in-part of the pending application by the same inventor entitled: SURGICAL/ANESTHESIA SUCTION DEVICE WITH NOISE-CONTROL VALVE, Ser. No. 06/854,551 filed on Apr. 21, 1986 now abandoned.

BACKGROUND

Previous arts of suction aspirators consist of a suction tube with or without an interrupting valve. These valves are mainly incorporated to control the vacuum suction flow and obviously, the control of suction noise is inefficient.

U.S. Pat. No. 2,650,792 by Marco (C1L2,3) "A valve employed for controlling flow of a liquid or semi-solid materials". (C5-L58): "A valve for mixing apparatus . . . ." U.S. Pat. No. 3,998,227 by Holbrook et al: (C1-L65,66): "A new and improved regulator for fluids aspiration systems" from which the suction noise is not completely eliminated: (C2-L12,13: "A minimum or no noise generating capacity".

U.S. Pat. No. 4,610,664 by Harle: (C2-L46,47,48,49) using different valve mechanism mainly for one-handed operation.

U.S. Pat. No. 3,517,669 by Bouno et al: (C1-L13,14): "A valve for eliminating suction forces at a catheter tip". (C4-L1,2): "even the catheter port is closed, the atmospheric port is open to the suction source".

U.S. Pat. No. 3,335,727 by Victor T Spoto: "A valve controlled suction device through which the flow of blood may be controlled", (C3-L14,15): "The provision of a vent passage on the downstream side of the valve assembly".

SUMMARY

To overcome the shortcomings of the existing arts, the present invention is focusing on a simply constructed valve to control simultaneously the vacuum suction noise and the suction flow: the said valve is incorporated to the suction device in such it can be operated by a single hand so that, in this manner, the other hand of the operator is free for different task; the said suction device is unencumbered for sterilization to be used by the surgeon during surgical procedure.

BRIEF DESCRIPTION OF THE DRAWINGS

FIG. 1 is a perspective view of the invention is cylindrical in construction and is perpendicularly intersected with the handle (21) of the suction device.

(25): The interrupting valve key is seen by its upper portion.

(26): A turning knob incorporated with the valve structure to help rotating the valve inside the adaptor body.

FIG. 2 Illustrates the suction device with the interrupting valve having been rotated to the open position.

FIG. 3 Illustrates the suction device with the interrupting valve having been rotated to the closed position.

Figure 4A:
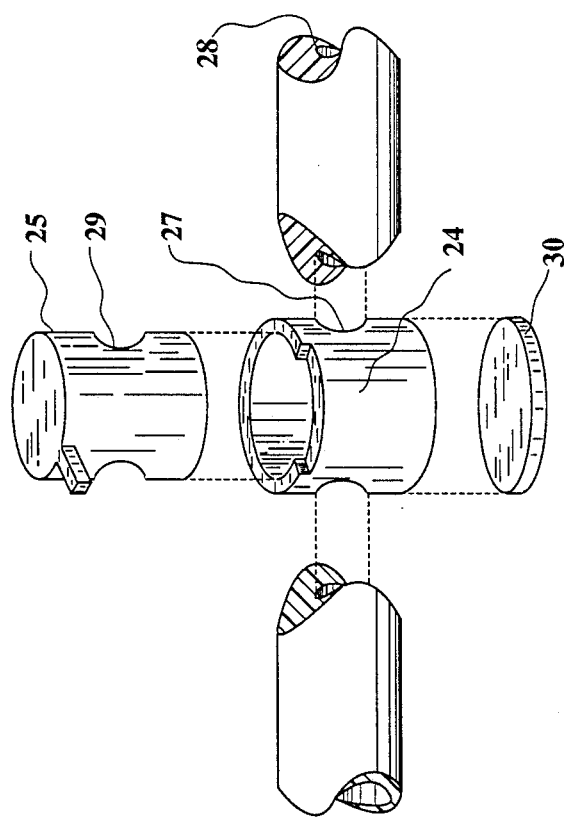
Figure 4B:
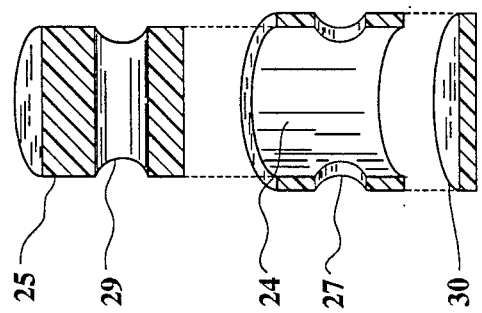

FIG. 4 and cross section of FIG. 4 illustrate the anatomy of the valve mechanism.

Figure 5:
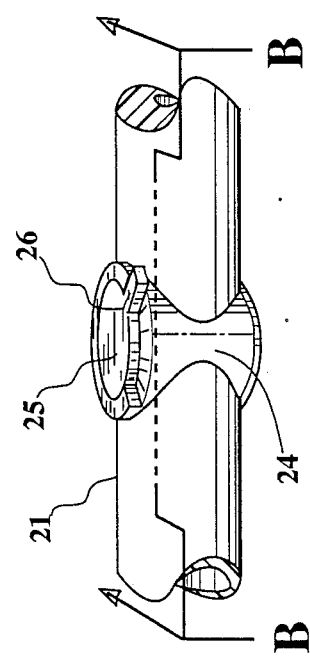

FIG. 5 Similar to FIG. 3. This figure is to help explaining the sectional structure of the interrupting valve when it is in closed position.

Figure 6:
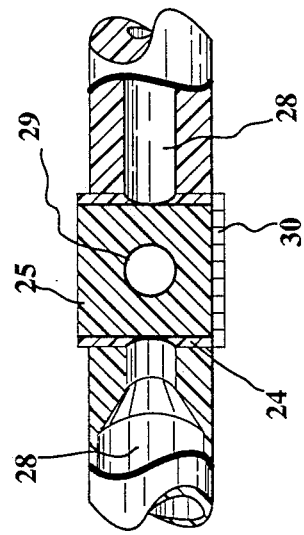

FIG. 6 Frontal sectional view of the suction device at the level of the valve. The valve passage is seen in closed position.

Figure 7:
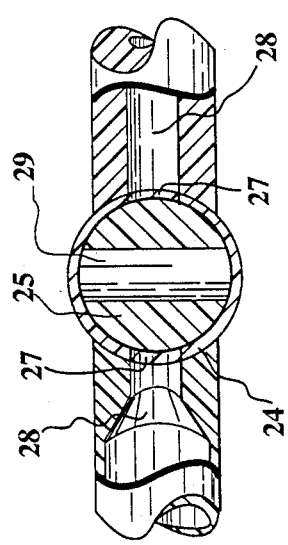

FIG. 7 Horizontal sectional view of the suction device at the level of the valve. The valve passage is seen in closed position.

Figure 8:
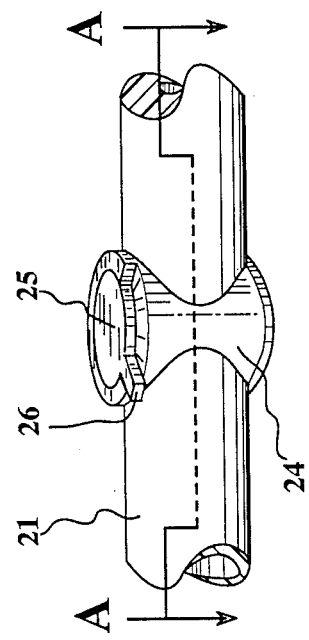

FIG. 8 Similar to FIG. 2. This figure is to help explaining the sectional structures of the interrupting valve when it is in open position.

Figure 9:
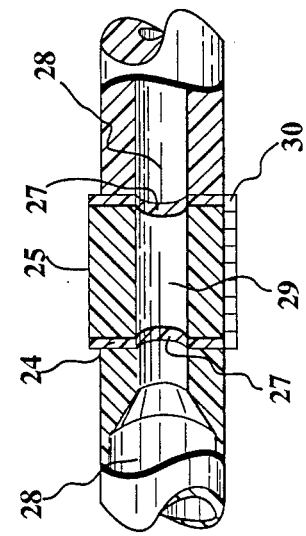

FIG. 9 Frontal sectional view of the suction device at the level of the valve. The valve passage is seen in open position.

Figure 10:
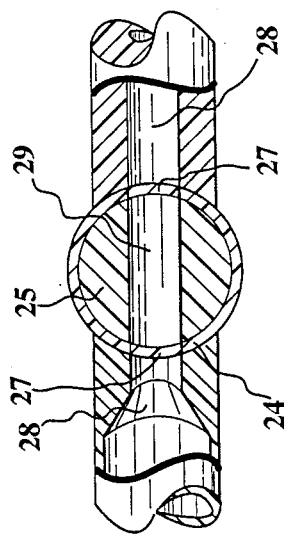

FIG. 10 Horizontal sectional view of the suction device at the level of the valve. The valve passage is seen in open position.

DESCRIPTION OF THE PREFERRED EMBODIMENTS

Referring now to the drawings and in particular to FIG. 1, the suction apparatus is represented with the suction tip(22), suction handle(21) and suction port(23). The apparatus is cylindrical so that the tubular suction passage is provided. The suction passage is interrupted at the handle level of the suction device by a valve structure. The said interrupting valve structure (25) is seated inside of the adaptor body(24) which inturn, is cylindrical construction providing a cooperating structure on both the body and the valve structure to allow a rotation of the valve structure within the body. The said adaptor body is perpendicularly intersected with the suction device at the handle level. The bottom plate (30) is in circular construction with an equal diameter with the outer diameter of the adaptor body (24) and is glued to the bottom end of the valve structure in order to allow the valve to rotate inside of the adaptor and to keep the valve from falling out of the adaptor FIG. 2 and FIG. 3 demonstrate a structure of the upper open of the adaptor body for limiting the turning knob(26) to rotate within substantially a quarter turn. The suction can be brought into its working position by using the hand holding the suction device at its handle (21); The operator uses the finger or the thumb of the same hand to push forward the turning knob, thus, the valve passage(29) is rotated to align itself with the suction passage(28) to allow an unrestricted vacuum suction flow to establish between the suction tip(22) and suction source which has been connected to the device at its suction port (23). The suction vacuum is progressively obstructed when the rotating knob(26) is pulled backward, thus, the valve passage is rotated away from the suction passage(28) to form a physical blockade to the vacuum suction flow. In this position, the suction flow is temporary and physically blocked and the suction noise is eliminated. This is one of the structural feature of this invention: Using the valve structure to provide a passage for the suction system at one time and using the same valve structure at another time to block the suction flow and to eliminate effectively the suction noise. FIG. 4 also demonstrates a structural incorporation between the turning knob (26) and the valve passage (29) of the interrupting valve: It is so constructed that, when the turning knob(26) is pushed forward to one limit extreme, the valve passage (29) is rotated to align with the elongated suction passage(28); and when the turning knob(26) is pulled backward to the other limit extreme, the valve passage(29) is rotated away from the suction passage(28). Between the two limit extremes, the turning knob and therefore the valve passage can be stopped and can stay at any position to provide a partial opening of the vacuum suction flow; for this reason, the valve structure is unbiased to any working position with the suction device.

While particular embodiments of the invention have been shown and described, it will be obvious to those skilled in the art the various changes and modifications which may be made without departing from the essential features of the present invention and, therefore, the aim in the appended claims is to cover all such changes and modifications as fall within the true spirit and scope of the invention.

What is claimed as new is as follows:

1. In combination with a flexible conduit adapted to be connected to a vacuum source for inducing a flow therethrough, a noise control valve device for controlling suctioning of liquids from a human body cavity, said valve controlled suction device improvement comprising a tubular elongated suction passage having a bore bisecting said suction passage, a cylindrical, hollow adaptor body positioned within said bisecting bore adapted to receive a rotatable valve plug member, said adaptor body having open and closed ends with a flange around the open end thereof, said flange having a cut out portion or recess thereon to limit rotary movement of the said valve member, said adaptor body further having inlet and outlet parts aligned with said suction passage, a rotatable valve plug member recited within said adaptor hollow body having a valve passage therein for alignment or misalignment with said adaptor parts, said valve body having a knob means thereon engaging within said flange cut out for limiting rotary movement thereof, so that rotary movement of the valve member alternately aligns or misaligns the valve passage with the suction passage to either open to unrestricted suction at one limit or restrict the suction completely at the other limit to effectively eliminate suction noise, whereby the improvement allows the operator to employ the suction device by himself with only one hand holding the suction device by its handle while using the thumb of finger of the one hand to operate the suction on/off by just moving said knob means within the flange cut out limit so that the other hand of the operator is free for a different task, said valve device being non-vented to the atmosphere in any position of the valve.

* * * * *